US00PP18488P3

(12) United States Plant Patent
Olesen

(10) Patent No.: US PP18,488 P3
(45) Date of Patent: Feb. 12, 2008

(54) SHRUB ROSE PLANT NAMED 'POULTC011'

(50) Latin Name: *Rosa hybrida*
Varietal Denomination: Poultc011

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/389,465

(22) Filed: Mar. 23, 2006

(65) Prior Publication Data

US 2007/0226844 P1 Sep. 27, 2007

(51) Int. Cl.
*A01H 5/00* (2006.01)

(52) U.S. Cl. ..... Plt./108

(58) Field of Classification Search ..... Plt./108
See application file for complete search history.

*Primary Examiner*—Kent Bell
*Assistant Examiner*—Louanne Krawczewicz Myers

(57) ABSTRACT

A new garden rose plant of the shrub class which has abundant, red flowers and attractive foliage. This new and distinct variety has shown to be uniform and stable in the resulting generations from asexual propagation.

1 Drawing Sheet

Botanical classification: *Rosa hybrida.*
Variety denomination: 'Poultc011'.

SUMMARY OF THE CLAIMED PLANT

The present invention constitutes a new and distinct variety of garden rose plant which originated from a controlled crossing between the female seed parent plant, an unnamed seedling (non-patented), and the male pollen parent plant, an unnamed seedling (non-patented). The two parents were crossed during the summer of 1997, and the resulting seeds were planted in a controlled environment in Fredensborg, Denmark. The new variety is named 'Poultc011'.

The new variety may be distinguished from its female seed parent, by the following combination of characteristics:

1. 'Poultc011 has of low growth height ranging from 40 to 60 cm. The female parent plant is less compact, growing to 100 cm in height.
2. 'Poultc011' exhibits flowers with a smaller diameter than those of the unnamed female parent.
3. 'Poultc011' develops more flower buds than observed on the seed parent.

The new variety may be distinguished from its pollen parent by the following combination of characteristics:

1. The claimed plant has slightly larger flowers than the pollen parent.
2. 'Poultc011' bears flower buds in larger clusters than observed on the pollen parent plant.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance; and
4. Suitability for rose container culture.

This combination of qualities is not present in previously available commercial cultivars of this type, known to the inventor, and distinguish 'Poultc011' from all other varieties of which we are aware.

As part of the rose development program, Mogens N. Olesen germinated the seeds from the aforementioned hybridization during winter of 1997 and conducted evaluations on the resulting seedlings in a controlled environment in Fredensborg, Denmark.

'Poultc011' was selected in the spring 1998 by the inventor as a single plant from the progeny of the aforementioned hybridization.

Asexual reproduction of 'Poultc011' by traditional budding and rooted cuttings was first done by Mogens N. Olesen in the nursery in Fredensborg, Denmark in July, 1998. This initial and other subsequent asexual propagations conducted in controlled environments have demonstrated that the characteristics of 'Poultc011' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poultc011'. Specifically illustrated in the drawing.

DETAILED DESCRIPTION OF THE VARIETY

Figures 1A, 1B, 1C, 1D, 1E, 1F:
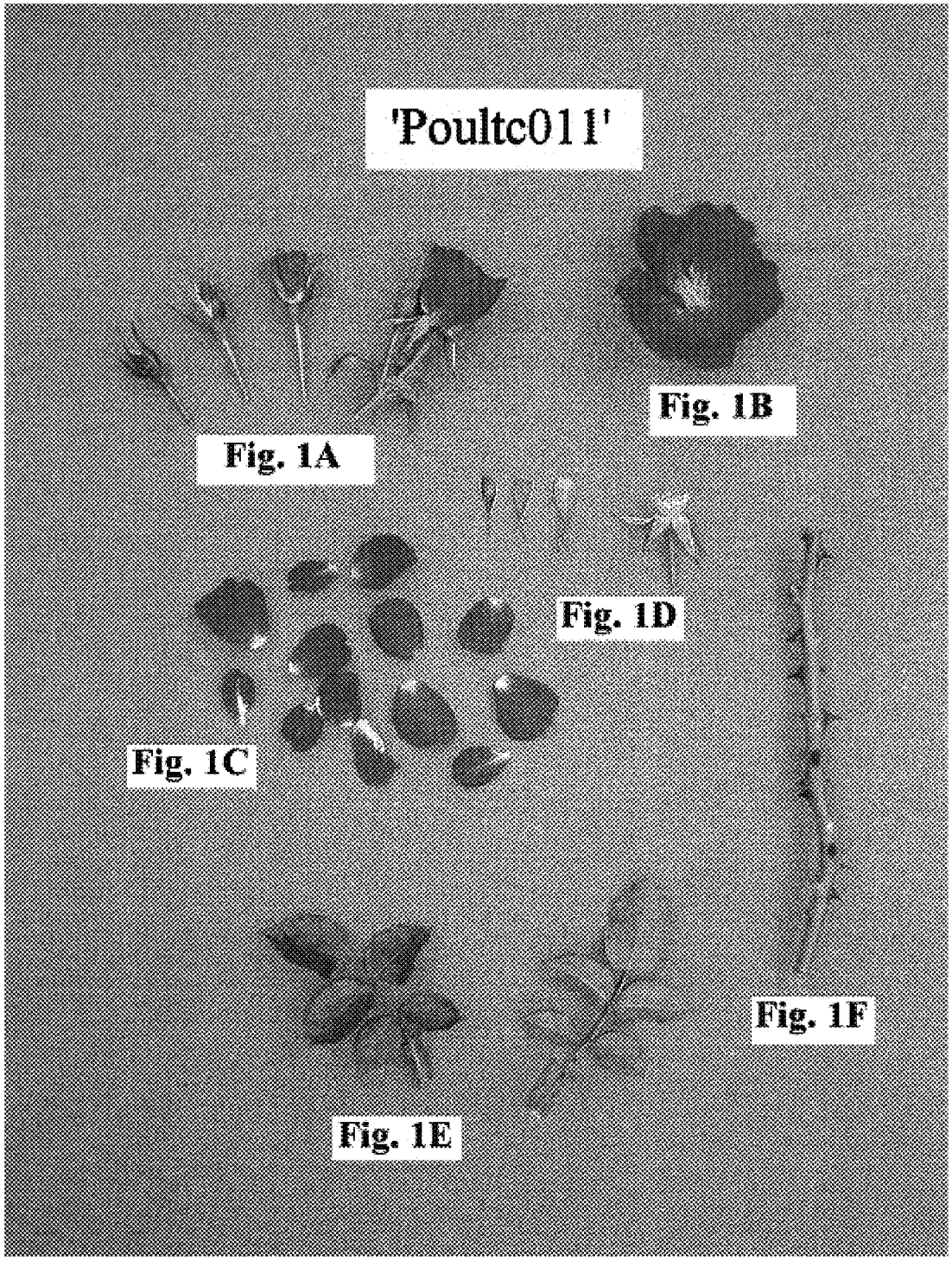
FIG. 1A; Flower bud closed, flower bud as sepals unfold, and partially open.
FIG. 1B; Open flower.
FIG. 1C; Flower petals and petaloids, detached.
FIG. 1D; Sepals, receptacle, and peduncle.
FIG. 1E; Mature leaves.
FIG. 1F; Bare stem exhibiting prickles.

The following is a description of 'Poultc011', as observed in its growth in a field nursery in Odense Denmark. Observed plants are 3 years of age, grown on *Rosa multiflora* understock. Color references are made using The Royal Horticultural Society (London, England) Colour Chart, 2001, except where common terms of color are used.

For a comparison, several physical characteristics of the rose variety 'Poulharmu', a rose variety from the same inventor described and illustrated in U.S. Plant Pat. No. 12,681, are compared to 'Poultc011' in Chart 1.

CHART 1

| | 'Poultc011' | 'Poulharmu' |
|---|---|---|
| Average flower diameter | 55 mm | 45 mm |
| Filament color | Yellow Group 7B | Yellow-Green Group 154D on lower portion, changing to Greyed-Orange Group 163B at the upper portion |
| General color of open flower | Red Group 45B to 46C. | Red Group 44B |

FLOWER AND FLOWER BUD

Blooming habit: Continuous.

Flower bud:

*Size.*—Upon opening, 20 mm in length from base of receptacle to end of bud. Diameter is 9 mm.

*Bud form.*—Pointed ovate.

*Bud color.*—As sepals unfold petals are Red Group 45C. Sepal Upper Surface: Color: Yellow-Green Group 146B. Surface: Weak to medium pubescence observed. Sepal Lower Surface: Color: Yellow-Green Group 144A. Anthocyanic pigments of Greyed-Purple Group 183A. Texture: Smooth with few stipitate glands. Sepal Shape: Sepals are lanceolate. Apex is cirrhose. Base is flat at union with receptacle. Sepal Margin: Margins have very weak foliaceous appendages on three of the five sepals. Size: Normally 21 mm (l)×6 mm (w).

*Receptacle.*—Surface: Smooth. Shape: Pear shaped. Size: 6 mm (h)×5.5 mm (w). Color: Green Group 143A. Strong anthocyanic pigments the color of Greyed-Purple Group 183A observed.

*Pedicel.*—Surface: Rough with stipitate glands. Length: 15 to 25 mm average length. Diameter: 2 mm on average. Color: Yellow-Green Group 145B. Strong anthocyanic pigments the color of Greyed-Red Group 182A observed. Strength: Somewhat strong.

*Borne.*—In clusters or corymbs with 5 flowers per stem.

*Peduncles.*—Smooth in texture. Normally 3 to 5 cm in length from branch point with stem to the flower cluster. Diameter is typically 2 mm. Coloration is Yellow-Green Group 145 B.

Flower bloom:

*Fragrance.*—None.

*Duration.*—The blooms have a duration on the plant of approximately 7 days. Afterwards, petals fall cleanly away from plant.

*Size.*—Normally flower diameter is 55 mm when open. Depth is 23 mm.

*Form.*—General shape is a semi-double open cup.

*Shape of flower when viewed from the side.*—Upon opening, upper part: Flat. Upon opening, lower part: Flat. Open flower, upper part: Flattened convex. Open flower, lower parts: Flattened concave.

*Petalage.*—12 petals with 2 petaloids.

Color:

*Petals, upon and after opening.*—Outer side: Red Group 45B to 46C. Inner side: Red Group 53C with intonations of Red-Purple Group 58B.

*Basal petal spots.*—Outer side: Yellow Group 2C. Inner side: Yellow Group 2C to 2D.

General tonality: On open flower Red Group 45B to Red Group 46B.

Petals:

*Petal reflex.*—None, petals are generally flat.

*Margin.*—Entire. Moderate undulations of margin observed.

*Shape.*—Generally broad elliptical. Apex: Rounded. Base: Acute.

*Size.*—30 mm (l)×31 mm (w).

*Texture.*—Smooth.

*Thickness.*—Average.

Petaloids:

*Quantity.*—On average, 2.

*Color.*—Red Group 45B to 46C on the outer surface. The inner surface is Red Group 53C with intonations of Red-Purple Group 58B. Basal petal spots are Yellow Group 2C on the outer side. The inner side petal spots are Yellow Group 2C to 2D.

*Size.*—Normally 22 mm (l)×8 mm (w).

Reproductive organs:

*Pistils.*—Length: Normally 5 mm. Quantity: 40 on average.

*Pollen.*—None observed.

*Anthers.*—Size: 2 mm in length. Color: Yellow Group 11B at center and Yellow Group 12A at margins. Quantity: 95 on average.

*Filaments.*—Color: Yellow Group 7B. Length: Normally 6 mm.

*Stigma.*—Superior in location relative to the length of the filaments and the height of the suspended anthers. Color: Yellow-Green Group 145D.

*Styles.*—Color: Yellow-Green Group 145D at base with Greyed-Red Group 180D.

*Hips.*—None Observed.

PLANT

Plant growth: Upright to bushy. When grown as a budded field grown plant on *Rosa multiflora* understock, the average height of the plant is 40 to 60 cm. Average spread is 50 cm.

Stems:

*Color.*—Juvenile wood: Yellow-Green Group 146B to Yellow-Green Group 145A. Older wood: Yellow-Green Group 146B.

*Length.*—Normally 30 to 35 cm from the base of the stem to the flowering position.

*Diameter.*—5 to 6 mm.

*Internodes.*—15 to 25 mm.

*Surface texture.*—Young wood: Smooth. Older wood: Smooth.

Prickles:

*Incidence.*—11 prickles per 10 cm of stem.

*Color.*—Juvenile prickles: Greyed-Purple Group 183B. Mature prickles: Greyed-Purple Group 183C.

*Shape.*—Upper side: Concave. Lower side: Deeply concave.

*Length.*—8 mm from base to apex. 9 mm wide.

Plant foliage: Normal number of leaflets on normal leaves in middle of the stem: 5 leaflets.

*Compound leaf size.*—On average, 90 mm (l)×55 mm (w).

*Quantity.*—5 leaves per 10 cm of stem on average.

*Color.*—Mature foliage: Upper surface: Yellow-Green Group 147A. Lower surface: Yellow-Green Group 147B. Juvenile foliage: Upper surface: Yellow-Green Group 146A. Lower surface: Yellow-Green Group 146B.

Plant leaves and leaflets:

*Stipules.*—Size: 15 to 20 mm in length. Margins: Finely serrated with many stipitate glands. Color: Yellow-Green Group 147A.

*Petiole.*—Length: Normally 27 mm. Diameter: 2 mm average. Upper surface: Color: Greyed-Red Group 182A. Lower surface: Color: Yellow-Green Group 146C.

*Rachis.*—Length: Normally 25 mm. Above: Color: Yellow-Green Group 147A with anthocyanic intonations of Greyed-Purple 183A. Underneath: Color: Yellow-Green Group 146C. Observations: Few stipitate glands and small prickles observed. Small prickles are Greyed-Red 181A in color.

*Leaflet.*—Size: Normally 33 mm (l)×23 mm (w). Edge: Finely serrated. Shape: Elliptical to orbicular. Base: Rounded. Apex: Acuminate. Texture: Smooth. Thickness: Average. Arrangement: Odd pinnate. Venation: Reticulate. Glossiness: Somewhat glossy.

Disease resistance: Above average resistance to powdery and downy mildew, rust, black spot, and *Botrytis* under normal growing conditions in Jackson County, Oreg.

Cold hardiness: The variety 'Poultc011' has been found tolerant to USDA Cold Hardiness Zone 6.

It is claimed:

1. A new and distinct variety of rose plant of the shrub rose class named 'Poultc011', substantially as illustrated and described herein, due to its abundant red flowers, disease resistance, and extended period of bloom.

* * * * *

'Poultc011'